(12) United States Patent
Lui et al.

(10) Patent No.: US 8,288,582 B2
(45) Date of Patent: Oct. 16, 2012

(54) METHOD FOR THE PRODUCTION OF 2-FLUOROACYL-3-AMINOACRYLIC ACID DERIVATIVES

(75) Inventors: Norbert Lui, Odenthal (DE); Thomas Wollner, Köln (DE); Jürgen Wieschmeyer, Bergisch Gladbach (DE); Michael Dockner, Köln (DE); Jens-Dietmar Heinrich, Burscheid (DE)

(73) Assignee: Bayer CropScience AG, Monheim (DE)

( * ) Notice: Subject to any disclaimer, the term of this patent is extended or adjusted under 35 U.S.C. 154(b) by 55 days.

(21) Appl. No.: 12/809,830

(22) PCT Filed: Dec. 16, 2008

(86) PCT No.: PCT/EP2008/010689
§ 371 (c)(1),
(2), (4) Date: Jun. 21, 2010

(87) PCT Pub. No.: WO2009/083134
PCT Pub. Date: Jul. 9, 2009

(65) Prior Publication Data
US 2010/0274049 A1 Oct. 28, 2010

(30) Foreign Application Priority Data
Dec. 21, 2007 (EP) ..................................... 07150357

(51) Int. Cl.
*C07C 229/30* (2006.01)
(52) U.S. Cl. ....................................................... 560/170
(58) Field of Classification Search ........................ None
See application file for complete search history.

(56) References Cited

U.S. PATENT DOCUMENTS

| 5,401,869 A | 3/1995 | Kraus et al. |
| 6,207,828 B1 | 3/2001 | Osei-Gyimah |
| 6,706,911 B1 | 3/2004 | Lui et al. |
| 2001/0025109 A1 * | 9/2001 | Drauz et al. .................. 548/413 |
| 2006/0252944 A1 | 11/2006 | Lantzsch et al. |
| 2007/0225280 A1 | 9/2007 | Anderson et al. |

FOREIGN PATENT DOCUMENTS

| WO | WO 03/051820 A1 | 6/2003 |
| WO | WO 2005/042468 A1 | 5/2005 |

OTHER PUBLICATIONS

Knoll & Co, Journal of the Chemical Society, Abstract 80, I, p. 703, 1901.).*
Bartnik, R., et al., "A New Synthesis of Enaminoketones," *Tetrahedron Letters* 37(48):8751-8754, Elsevier Science Ltd., England (1996).
Hojo, M., et al., "Electrophilic Substitutions of Olefinic Hydrogens II. Acylation of Vinyl Ethers and N-Vinyl Amides," *Chemistry Letters* 499-502, Chemical Society of Japan, Japan (1976).
Rene, L., et al., "A One Pot Synthesis of β-Cyanoenamines," *Synthesis* 5:419-420, Thieme Chemistry, Germany (1989).
International Search Report for International Application No. PCT/EP2008/010689, European Patent Office, Netherlands, mailed on Mar. 20, 2009.

* cited by examiner

*Primary Examiner* — Paul A Zucker
(74) *Attorney, Agent, or Firm* — Sterne, Kessler, Goldstein & Fox P.L.L.C.

(57) ABSTRACT

The present invention relates to a process for preparing 2-fluoroacyl-3-aminoacrylic acid derivatives by reacting fluorinated carboxylic acids with dialkylaminoacrylic acid derivatives and acid halides.

10 Claims, No Drawings

METHOD FOR THE PRODUCTION OF 2-FLUOROACYL-3-AMINOACRYLIC ACID DERIVATIVES

The present invention relates to a process for preparing 2-fluoroacyl-3-aminoacrylic acid derivatives by reacting fluorinated carboxylic acids with dialkylaminoacrylic acid derivatives and acid halides.

2-Fluoroacyl-3-aminoacrylic acid derivatives, for example 2-trifluoromethyl-3-aminoacrylic esters and 2-difluoromethyl-3-aminoacrylic esters, are valuable intermediates for preparing substituted pyrazoles, which may find use as fungicides.

It is already known that trihaloacylated aminoacrylic esters are obtained when the corresponding chloroacroleins are reacted with a substituted amine (cf. Tetrahedron Lett. 1996, 37, 8751-8754). However, a disadvantage of this process is that the chloroacroleins used as starting compounds are difficult to prepare and are too expensive for an industrial application.

EP-A-1 000 926 discloses that trihaloacylaminopropenoates are obtained by reacting trihaloacetoacetates with dialkylformamide acetals. A disadvantage here is that the deacylated compounds occur as by-products and have to be removed from the desired product.

WO-A-03/051820 discloses that 2-perhaloacyl-3-aminoacrylic acid derivatives can be obtained by reacting 3-aminoacrylic esters with perhaloalkylcarboxylic anhydrides. A disadvantage here is that the preparation of the fluorinated derivatives requires low-boiling and expensive acid chlorides or anhydrides. In the case of use of, for example, trifluoroacetic anhydride, one equivalent of the valuable fluorinated unit is lost.

WO-A-05/042468 teaches a process for preparing 2-dihaloacyl-3-aminoacrylic esters, in which acid halides are used. These acid chlorides are complicated to prepare from the acids. Moreover, their use is difficult owing to the low boiling points.

It was an object of the present invention to provide novel, economically viable processes for preparing 2-fluoroacyl-3-aminoacrylic acid derivatives proceeding from fluorinated carboxylic acids, which do not have the above-described disadvantages.

The object was achieved in accordance with the present invention by a process for preparing 2-fluoroacyl-3-aminoacrylic acid derivatives of the general formula (I)

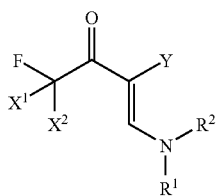

(I)

in which $R^1$ and $R^2$ are each independently selected from $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; or $R^1$ and $R^2$, together with the nitrogen atom to which they are bonded, may form a 5- to 6-membered ring which may optionally contain one or two further heteroatoms selected from O, S and an $SO_2$ group, and which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;

Y is selected from (C=O)OR$^3$, CN and (C=O)NR$^4$R$^5$, where R$^3$, R$^4$ and R$^5$ are each independently selected from $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl- and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; and $X^1$ and $X^2$ are each independently fluorine, chlorine, bromine, hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl or $C_{7-19}$-alkylaryl groups, where the aforementioned alkyl, cycloalkyl, alkenyl, alkynyl, aryl, aryl-alkyl and alkylaryl groups may each be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;

characterized in that
fluorinated carboxylic acids of the formula (II)

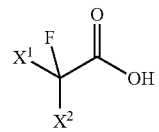

(II)

in which $X^1$ and $X^2$ are each as defined above
are reacted with 3-aminoacrylic acid derivatives of the formula (III)

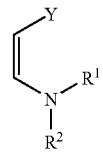

(III)

in which $R^1$, $R^2$ and Y are each as defined above,
and, in the presence of a base, with an acid halide of the formula (IV)

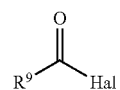

(IV)

in which
R$^9$ is selected from $C_{1-12}$-alkyl, $C_{3-8}$-cycloalkyl, $C_{2-12}$-alkenyl, $C_{2-12}$-alkynyl, $C_{6-8}$ aryl, $C_{7-19}$-arylalkyl- or $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a C$_{1-12}$-alkyl group;

Hal is halogen.

It is surprisingly possible to prepare the 2-fluoroacyl-3-aminoacrylic acid derivatives of the formula (I) under the inventive conditions with good yields and in high purity, which means that the process according to the invention does not have the disadvantages described in connection with the prior art.

The process according to the invention can be explained by the following scheme (I):

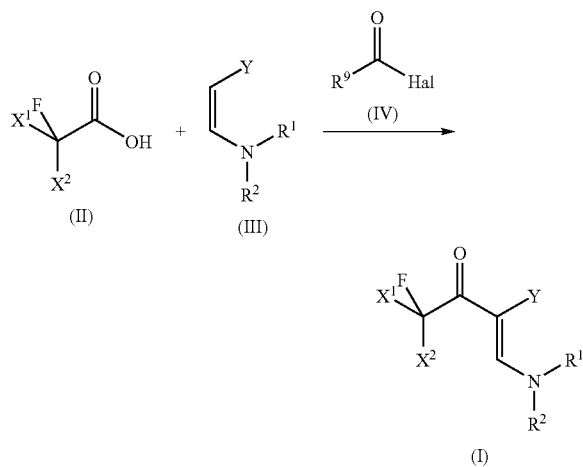

Scheme (I)
General Definitions

In connection with the present invention, the term "halogens" (X), unless defined otherwise, encompasses those elements which are selected from the group consisting of fluorine, chlorine, bromine and iodine, preference being given to using fluorine, chlorine and bromine, and particular preference to using fluorine and chlorine.

Optionally substituted groups may be mono- or polysubstituted, the substituents being identical or different in the case of polysubstitutions.

Alkyl groups substituted by one or more halogen atoms (—X) are, for example, selected from trifluoromethyl (CF$_3$), difluoromethyl (CHF$_2$), CF$_3$CH$_2$, ClCH$_2$, CF$_3$CCl$_2$.

In connection with the present invention, unless defined otherwise, alkyl groups are linear or branched hydrocarbon groups which may optionally have one, two or more heteroatoms selected from O, N, P and S. In addition, the inventive alkyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a C$_{1-12}$-alkyl group, preferably a C$_{2-10}$-alkyl group, more preferably a C$_{3-8}$-alkyl group, which may have one or more heteroatoms selected from N, O, P and S.

In connection with the present invention, unless defined otherwise, cycloalkyl groups are monocyclic, saturated hydrocarbon groups which have 3 to 8 carbon ring members and may optionally have one, two or more heteroatoms selected from O, N, P and S. In addition, the inventive cycloalkyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a C$_{1-12}$-alkyl group, preferably a C$_{2-10}$-alkyl group, more preferably a C$_{3-8}$-alkyl group, which may have one or more heteroatoms selected from N, O, P and S.

Specifically, this definition encompasses, for example, the meanings of cyclopropyl, cyclobutyl, cyclopentyl and cyclohexyl.

The C$_1$-C$_{12}$-alkyl definition encompasses the largest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined otherwise, alkenyl groups are linear or branched hydrocarbon groups which contain at least one single unsaturation (double bond) and may optionally have one, two or more single or double unsaturations or one, two or more heteroatoms selected from O, N, P and S. In addition, the inventive alkenyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a C$_{1-12}$-alkyl group, preferably a C$_{2-10}$-alkyl group, more preferably a C$_{3-8}$-alkyl group, which may have one or more heteroatoms selected from N, O, P and S.

The C$_2$-C$_{12}$-alkenyl definition encompasses the largest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In connection with the present invention, unless defined otherwise, cycloalkenyl groups are monocyclic, nonaromatic hydrocarbon groups which have 3 to 8 carbon ring members and at least one double bond, and which may optionally have one, two or more heteroatoms selected from O, N, P and S. In addition, the inventive cycloalkenyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a C$_{1-12}$-alkyl group, preferably a C$_{2-10}$-alkyl group, more preferably a C$_{3-8}$-alkyl group, which may have one or more heteroatoms selected from N, O, P and S.

Specifically, this definition encompasses, for example, the meanings of cyclopenten-1-yl, cyclohexen-1-yl, cyclohepta-1,3-dien-1-yl.

In connection with the present invention, unless defined otherwise, alkynyl groups are linear, branched or cyclic hydrocarbon groups which contain at least one double unsaturation (triple bond) and may optionally have one, two or more single or double unsaturations or one, two or more heteroatoms selected from O, N, P and S. In addition, the inventive alkynyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a linear, branched or cyclic $C_{1-12}$-alkyl group, which may have one or more heteroatoms selected from N, O, P and S.

The $C_2$-$C_{12}$-alkynyl definition encompasses the largest range defined herein for an alkynyl group. Specifically, this definition encompasses, for example, the meanings of ethynyl (acetylenyl); prop-1-ynyl and prop-2-ynyl.

In connection with the present invention, unless defined otherwise, aryl groups are aromatic hydrocarbon groups which may have one, two or more heteroatoms selected from O, N, P and S and may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably a $C_{2-10}$-alkyl group, more preferably a $C_{3-8}$-alkyl group, which may have one or more heteroatoms selected from N, O, P and S.

The $C_{5-18}$-aryl definition encompasses the largest range defined herein for an aryl group having 5 to 18 skeleton atoms, where the carbon atoms may be exchanged for heteroatoms. Specifically, this definition encompasses, for example, the meanings of cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In connection with the present invention, unless defined otherwise, arylalkyl groups (aralkyl groups) are alkyl groups which are substituted by aryl groups and may have a $C_{1-8}$-alkylene chain and may be substituted in the aryl skeleton or the alkylene chain by one or more heteroatoms selected from O, N, P and S and optionally by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably a $C_{2-10}$-alkyl group, more preferably a $C_{3-8}$-alkyl group, which may have one or more heteroatoms selected from N, O, P and S.

The $C_{7-19}$-aralkyl group definition encompasses the largest range defined herein for an arylalkyl group having a total of 7 to 19 atoms in the skeleton and alkylene chain. Specifically, this definition encompasses, for example, the meanings of benzyl and phenylethyl.

In connection with the present invention, unless defined otherwise, alkylaryl groups (alkaryl groups) are aryl groups which are substituted by alkyl groups and may have a $C_{1-8}$-alkylene chain and may be substituted in the aryl skeleton or the alkylene chain by one or more heteroatoms selected from O, N, P and S and optionally by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably a $C_{2-10}$-alkyl group, more preferably a $C_{3-8}$-alkyl group, which may have one or more heteroatoms selected from N, O, P and S.

The $C_{7-19}$-alkylaryl group definition encompasses the largest range defined herein for an alkylaryl group having a total of 7 to 19 atoms in the skeleton and alkylene chain. Specifically, this definition encompasses, for example, the meanings of tolyl, 2,3-, 2,4-, 2,5-, 2,6-, 3,4- or 3,5-dimethylphenyl.

The alkyl, alkenyl, alkynyl, aryl, alkaryl and aralkyl groups may additionally have one or more heteroatoms which—unless defined otherwise—are selected from N, O, P and S. In that case, the heteroatoms replace the numbered carbon atoms.

The inventive compounds may optionally be present in the form of mixtures of different possible isomeric forms, especially of stereoisomers, for example E and Z, threo and erythro, and also optical isomers, but if appropriate also of tautomers. Both the E and the Z isomers, and the threo and erythro isomers, and the optical isomers, any mixtures of these isomers, and the possible tautomeric forms are disclosed and claimed.

Dialkylaminoacrylic Acid Derivatives (III)

The dialkylaminoacrylic acid derivatives used as starting materials in the performance of the process according to the invention are defined in general terms by the formula (III).

In this formula, $R^1$ and $R^2$ may each independently be selected from $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; or $R^1$ and $R^2$, together with the nitrogen atom to which they are bonded, may form a 5- to 6-membered ring which may optionally contain one or two further heteroatoms selected from O, S and an $SO_2$ group;

Y may be selected from (C=O)OR$^3$, CN and (C=O)NR$^4$R$^3$, where R$^3$, R$^4$ and R$^5$ are each independently selected from $C_{1-12}$-alkyl, $C_{3-8}$-cycloalkyl, $C_{2-12}$-alkenyl, alkynyl, $C_{6-8}$-aryl, $C_{7-19}$-arylalkyl- and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group.

Preferably, $R^1$ and $R^2$ may each independently be selected from methyl, ethyl, n-propyl and isopropyl, or $R^1$ and $R^2$, together with the nitrogen atom to which they are bonded, may foul a piperidinyl, pyrrolidinyl or morpholidinyl ring;

Y may be selected from (C=O)OR$^3$ where R$^3$ is selected from methyl, ethyl, n-propyl and isopropyl.

More preferably,
R' and $R^2$ may each be methyl and
Y may be —(C=O)$OC_2H_5$.

Examples of dialkylaminoacrylic esters suitable in accordance with the invention are methyl 3-(N,N-dimethylamino)acrylate, ethyl 3-(N,N-dimethylamino)acrylate, ethyl 3-(N,N-diethylamino)acrylate, 3-(N,N-dimethylamino)acrylonitrile, N,N-dimethyl-3-(N,N-dimethylamino)acrylamide and N,N-diethyl-3-(N,N-dimethylamino)acrylamide, particular preference being given to ethyl 3-(N,N-di-methylamino)acrylate.

Processes for preparing dialkylaminoacrylic esters have been described before in the prior art, for example in EP-A-0 608 725.

Processes for preparing dialkylaminoacrylonitriles have been described in the prior art, for example by Rene et al. in Synthesis (1986), (5), 419-420.

The dialkylaminoacrylic acid derivatives may, if necessary, be purified, for example by distillation. However, this is generally not required in connection with the inventive reaction.

The molar ratio of dialkylaminoacrylic acid derivatives to fluorinated carboxylic acid used may, for example, be 0.5 to 3, preferably 0.8 to 2, more preferably 1.0 to 1.5.

Fluorinated Carboxylic Acids (II)

The fluorinated carboxylic acids used in accordance with the present invention are compounds of the general formula (II)

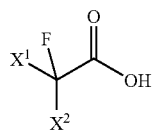

(II)

in which
$X^1$ and $X^2$ are each independently fluorine, chlorine, bromine, hydrogen, $C_{1-12}$-alkyl radicals, $C_{1-12}$-haloalkyl radicals, $C_{5-18}$-aryl, $C_{7-19}$-alkylaryl or $C_{7-19}$-arylalkyl radicals, preferably hydrogen, fluorine and chlorine, $C_{2-8}$-alkyl radicals, $C_{2-8}$-haloalkyl radicals, more preferably fluorine, chlorine, hydrogen, $C_{3-6}$-alkyl radicals, $CF_3$ and $CF_2H$.

Examples of fluorinated carboxylic acids suitable in accordance with the invention are trifluoroacetic acid, difluoroacetic acid, difluorochloroacetic acid, chlorofluoroacetic acid, 2,3,3,3-tetrafluoropropionic acid, 2,2,3,3-tetrafluoropropionic acid, 2,2-difluoropropionic acid, pentafluoropropionic acid, 2,3,3,4,4,4-hexafluorobutanecarboxylic acid.

Acid Halides (IV)

The above-described fluorinated carboxylic acids are reacted with the dialkylaminoacrylic acid derivative with addition of an acid halide of the formula (IV).

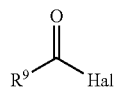

(IV)

In formula (IV), $R^9$ is selected from $C_{1-12}$-alkyl radicals, $C_{5-18}$-aryl, $C_{7-19}$-alkylaryl and $C_{7-19}$-arylalkyl or heteroaryl radicals, preferably from $C_{2-8}$-alkyl radicals, more preferably from $C_{3-6}$-alkyl radicals, and Hal is selected from fluorine, chlorine, bromine and iodine, preferably from chlorine and bromine, more preferably from chlorine.

Examples of acid halides suitable in accordance with the invention are acetyl chloride, pivaloyl chloride, isovaleroyl chloride and benzoyl chloride.

The molar ratio of acid halides of the formula (IV) to the fluorinated carboxylic acid of the formula (II) used may, for example, be 0.5 to 5, preferably 1 to 3, more preferably 2 to 2.5.

Bases

The process according to the invention is performed in the presence of a base. Suitable bases are, for example, tertiary nitrogen bases, for example tertiary amines, substituted or unsubstituted pyridines and substituted or unsubstituted quinolines; alkali metal or alkaline earth metal hydroxides, hydrogencarbonates or carbonates and other inorganic aqueous bases. Preference is given to using tertiary amines, substituted or unsubstituted pyridines, substituted or unsubstituted quinolines or substituted or unsubstituted imidazoles, and those of the general formula (V)

$$NR^{10}R^{11}R^{12}$$ (V)

in which
$R^{10}$, $R^{11}$ and $R^{12}$ are each independently $C_{1-12}$-alkyl, $C_{6-18}$-aryl, $C_{7-19}$-alkylaryl- or $C_{7-19}$-arylalkyl, or in each case two radicals together may also be part of a 5- to 8-membered N-heterocyclic radicals, or all three radicals together may be part of an N-heterobicyclic or N-tricyclic radical having 5 to 9 ring atoms per cycle, which may optionally also contain other heteroatoms, for example oxygen.

Preferred examples of bases of the general formula (V) are triethylamine, trimethylamine, diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3-, 4-picoline, 2-methyl-5-ethylpyridine, 2,6-lutidine, 2,4,6-collidine, 4-dimethylaminopyridine, quinoline, methylimidazole, ethylimidazole, butylimidazole, quinaldine, N,N,N,N-tetramethylethylenediamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN) and diazabicycloundecane (DBU). Preference is further given to alkali metal or alkaline earth metal hydroxides, carbonates or hydrogencarbonates, for example sodium hydroxide, potassium hydroxide, lithium hydroxide, calcium hydroxide, sodium carbonate, potassium carbonate, sodium hydrogencarbonate and potassium hydrogencarbonate. The inorganic base may optionally be used in the form of an aqueous solution in concentrations between 10 and 40%.

Particular preference is given to using triethylamine, tributylamine, methylimidazole, butylimidazole, pyridine, 2-, 3-, 4-picoline, 2-methyl-5-ethylpyridine, 2,6-lutidine, sodium hydroxide or potassium hydroxide.

The molar ratio of base to fluorinated carboxylic acid used may, for example, be 0.5 to 10, preferably 1 to 8, more preferably 1.5 to 6.

The use of greater amounts of base is uncritical but uneconomic.

The process according to the invention is performed, for example, at temperatures of −30 to 130° C., preferably between 10 and 60° C.

The process according to the invention is generally performed under standard pressure. However, it is possible to work under elevated pressure or in vacuo.

Solvents

The reaction can be performed in bulk or in a solvent. Preference is given to performing the reaction in a solvent.

Suitable solvents are, for example, selected from the group consisting of aliphatic and aromatic hydrocarbons, for example n-hexane, benzene, toluene and xylene, which may be substituted by fluorine and chlorine atoms, such as methylene chloride, dichloromethane, trichloromethane, carbon tetrachloride, fluorobenzene, chlorobenzene or dichlorobenzene; ethers, for example diethyl ether, diphenyl ether, methyl tert-butyl ether, isopropyl ethyl ether, dioxane, diglyme, dimethylglycol or THF; nitriles such as methyl nitrile, butyl nitrile or phenyl nitrile; DMF, N,N-dimethylacetamide, preference being given to toluene.

In a preferred embodiment of the process according to the invention, the base is initially charged with the fluorinated carboxylic acid in a solvent or in bulk, then the dialkylaminoacrylic acid derivative is added and admixed with the carbonyl chloride. It is also possible to initially charge the base with the carbonyl chloride in a solvent or in bulk, then to add the dialkylaminoacrylic acid derivative and admix with the fluorinated carboxylic acid.

In a further embodiment of the invention, the base is initially charged with the fluorinated carboxylic acid in a solvent or in bulk, then the carbonyl chloride is added and admixed with the dialkylaminoacrylic acid derivative.

Alternatively, the base can also replace the solvent. This is preferable especially when the salt of the base used is also liquid under the prevailing reaction conditions.

For the workup, the procedure may be, for example, to remove any precipitated salts, for example by filtration, centrifugation or sedimentation and decantation, and to either directly further react the reaction solution thus obtained or to obtain the 2-fluoroacyl-3-aminoacrylic acid derivatives by concentrating, preferably to dryness. If appropriate, the resulting 2-fluoroacyl-3-aminoacrylic acid derivatives may also be purified by distillation. A further workup method can be effected by addition of water to the reaction mixture and subsequent phase separation.

The process according to the invention for preparing 2-fluoroacyl-3-aminoacrylic acid derivatives is described in the examples which follow, which further illustrate the above description. However, the examples should not be interpreted in a limiting manner.

PREPARATION EXAMPLES

Example 1

To a solution of 32.7 g of triethylamine in 60 ml of toluene are added, at room temperature, first 11.6 g of difluoroacetic acid and then 14.35 g of ethyl dimethylaminoacrylate. 28 g of trimethylacetyl chloride are metered into this solution which is stirred at room temperature for 8 h. The reaction mixture is poured onto 30 ml of water, the organic phase is removed, the organic phase is washed with 20 ml of water, and the combined aqueous phases are extracted once again with 10 ml of toluene. The combined organic phases are concentrated under reduced pressure. This affords 21 g (94% of theory) of ethyl 2-(difluoroacetyl)-3-(dimethylamino)acrylate.

Example 2

To a solution of 17.8 g of triethylamine in 50 ml of toluene are added, at room temperature, first 5.7 g of trifluoroacetic acid and then 7.23 g of ethyl dimethylaminoacrylate. 14 g of trimethylacetyl chloride are metered into this solution which is stirred at room temperature for 6 h. The reaction mixture is poured onto 20 ml of water, the organic phase is removed, the organic phase is washed with 20 ml of water, and the combined aqueous phases are extracted once again with 10 ml of toluene. The combined organic phases are concentrated under reduced pressure. This affords 10.7 g (90% of theory) of ethyl 2-(trifluoroacetyl)-3-(dimethylamino)acrylate.

Example 3

To a solution of 17.8 g of triethylamine in 50 ml of toluene are added, at room temperature, first 4.8 g of difluoroacetic acid and then 7.23 g of ethyl dimethylaminoacrylate. 16.3 g of benzoyl chloride are metered into this solution which is stirred at room temperature for 6 h. The reaction mixture is filtered and poured onto 30 ml of water, the organic phase is removed, the organic phase is washed with 20 ml of water, and the combined aqueous phases are extracted once again with 10 ml of toluene. The combined organic phases are concentrated under reduced pressure. This affords ethyl 2-(difluoroacetyl-3-(dimethylamino)acrylate in a yield of 81%.

Example 4

To a solution of 298 g of 1-methyl-1H-imidazole in 560 ml of toluene are added, at room temperature (RT), first 97 g of difluoroacetic acid and then 144 g of ethyl dimethylaminoacrylate. 304 g of trimethylacetyl chloride are metered into this solution which is stirred at RT for 2 h. After the reaction has ended, the phases are separated, the lower phase is extracted once with 50 ml of toluene and the combined organic phases are concentrated under reduced pressure. This affords ethyl 2-(difluoroacetyl)-3-(dimethylamino)acrylate in a yield of 91%.

The invention claimed is:

1. A process for preparing a 2-fluoroacyl-3-aminoacrylic acid derivative of formula (I)

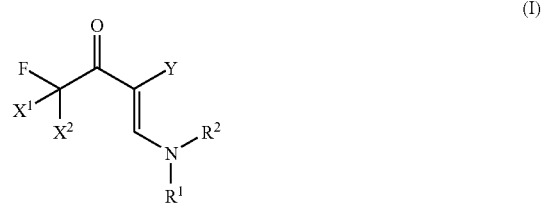

in which $R^1$ and $R^2$ are each independently selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; or $R^1$ and $R^2$, together with the nitrogen atom to which they are bonded, may form a 5- to 6-membered ring which may optionally contain one or two further heteroatoms selected from the group consisting of O, S and $SO_2$, and which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;

Y is selected from the group consisting of (C=O)OR$^3$, CN and (C=O)NR$^4$R$^5$, where R$^3$, R$^4$ and R$^5$ are each independently selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl- and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; and $X^1$ and $X^2$ are each independently fluorine, chlorine, bromine, hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl or $C_{7-19}$-alkylaryl groups, where the aforementioned alkyl, cycloalkyl, alkenyl, alkynyl, aryl, arylalkyl and alkylaryl groups may each be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;

comprising reacting a fluorinated carboxylic acid of formula (II)

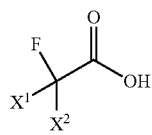
(II)

in which $X^1$ and $X^2$ are each as defined above, with a 3-aminoacrylic acid derivative of the formula (III)

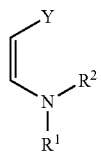
(III)

in which $R^1$, $R^2$ and Y are each as defined above, and, in the presence of a base, with an acid halide of the formula (IV)

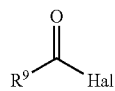
(IV)

in which $R^9$ is selected from the group consisting of $C_{1-12}$-alkyl, $C_{3-8}$-cycloalkyl, $C_{2-12}$-alkynyl, $C_{2-12}$-alkynyl, $C_{6-8}$-aryl, $C_{7-19}$-arylalkyl- and $C_{7-19}$-alkylaryl, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; and Hal is halogen.

2. A process for preparing a 2-fluoroacyl-3-aminoacrylic acid derivative of formula (I)

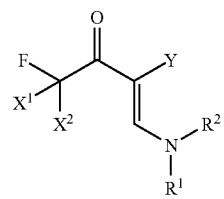
(I)

in which $R^1$ and $R^2$ are each independently selected from the group consisting of $C_{1-12}$-alkyl radicals, $C_{5-18}$-aryl, $C_{7-19}$-alkylaryl and $C_{7-19}$-arylalkyl radicals, or $R^1$ and $R^2$, together with the nitrogen atom to which they are bonded, may form a 5- to 6-membered ring which may optionally contain one or two further heteroatoms selected from the group consisting of O, S and SO$_2$, Y is selected from the group consisting of (C=O)OR$^3$, CN and (C=O)NR$^4$R$^5$, where R$_3$, R$_4$ and R$_5$ are each independently selected from the group consisting of $C_{1-12}$-alkyl radicals, $C_{5-18}$-aryl, $C_{7-19}$-alkylaryl and $C_{7-19}$-arylalkyl radicals and $X^1$ and $X^2$ are each independently fluorine, chlorine, bromine, hydrogen, $C_{1-12}$-alkyl radicals, $C_{1-12}$-haloalkyl radicals, $C_{5-18}$-aryl, $C_{7-19}$-alkylaryl or $C_{7-19}$-arylalkyl radicals, comprising reacting a fluorinated carboxylic acid of formula (II)

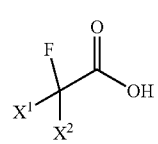
(II)

in which $X^1$ and $X^2$ are each as defined above, with a 3-aminoacrylic acid derivative of the formula (III)

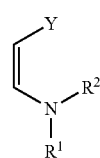
(III)

in which $R^1$, $R^2$ and Y are each as defined above, and, in the presence of a base, with an acid halide of the formula (IV)

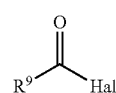
(IV)

in which $R^9$ is $C_{1-12}$alkyl, $C_{3-8}$-cycloalkyl, $C_{1-12}$-haloalkyl, $C_{5-18}$-aryl or $C_{7-19}$-arylalkyl; and Hal is halogen.

3. The process according to claim 1 or claim 2, wherein $R^1$ and $R^2$ are each independently selected from the group consisting of methyl, ethyl, n-propyl and isopropyl, or R¹ and R² together with the nitrogen atom to which they are bonded, form a piperidinyl or pyrrolidinyl ring;

Y is selected from (C=O)OR³ where R³ is selected from the group consisting of methyl, ethyl, n-propyl and isopropyl;

X¹ and X² are each independently selected from fluorine, chlorine, bromine and hydrogen;

Hal is chlorine or bromine; and

R⁹ is selected from $C_{1-12}$-alkyl.

4. The process according to claim 1 or claim 2, wherein R¹ and R² are each methyl,
Y is (C=O)OC₂H₅;
X¹ is fluorine;
X² is hydrogen;
Hal is chlorine and
R⁹ is methyl.

5. The process according to claim 1, wherein the fluorinated carboxylic acid is selected from the group consisting of trifluoroacetic acid, difluoroacetic acid, difluorochloroacetic acid, chlorofluoroacetic acid, 2,3,3,3-tetrafluoropropionic acid, 2,2,3,3-tetrafluoropropionic acid, 2,2-difluoropropionic acid, pentafluoropropionic acid, and 2,3,3,4,4,4-hexafluorobutanecarboxylic acid.

6. The process according to claim 5, wherein the dialkylaminoacrylic acid derivative is selected from the group consisting of methyl 3-(N,N-dimethylamino)-acrylate, ethyl 3-(N,N-dimethylamino)acrylate, ethyl 3 -(N,N-diethylamino)acrylate, 3-(N,Ndimethylamino)acrylonitrile, N,N-dimethyl-3-(N,N-dimethylamino)acrylamide and N,Ndiethyl-3-(N,N -dimethylamino)acrylamide.

7. The process according to claim 6, wherein the molar ratio of dialkylaminoacrylic acid derivative to fluorinated carboxylic acid used is 0.5 to 3.

8. The process according to claim 7, wherein the acid chloride is selected from acetyl chloride, pivaloyl chloride, isovaleroyl chloride and benzoyl chloride.

9. The process according to claim 8, wherein the molar ratio of acid chloride to the fluorinated carboxylic acid used is 0.5 to 5.

10. The process according to claim 9, wherein the base is selected from triethylamine, trimethylamine, diisopropylethylamine, tri-n-propylamine, tri-n-butylamine, tri-nhexylamine, tricyclohexylamine, N-methylcyclohexylamine, N-methylpyrrolidine, Nmethylpiperidine, N-ethylpiperidine, N,N-dimethylaniline, N-methylmorpholine, pyridine, 2-,3-,4-picoline, 2-methyl-5-ethylpyridine, 2,6-lutidine, 2,4,6-collidine, 4-dimethylaminopyridine, quinoline, methylimidazole, ethylimidazole, butylimidazole, quinaldine, N,N,N,N-tetramethylethylenediamine, N,N-dimethyl-1,4-diazacyclohexane, N,Ndiethyl-1,4-diazacyclohexane, 1,8-bis(dimethylamino)naphthalene, diazabicylooctane (DABCO), diazabicyclononane (DBN) and diazabicycloundecane (DBU), sodium hydroxide, potassium hydroxide, lithium hydroxide, calcium hydroxide, sodium carbonate, potassium carbonate, sodium hydrogencarbonate and potassium hydrogencarbonate.

\* \* \* \* \*